(12) United States Patent  
Klinberg et al.

(10) Patent No.: US 6,725,862 B2  
(45) Date of Patent: Apr. 27, 2004

(54) TRACHEOSTOMY TUBE APPARATUS FOR NONINVASIVE SUCTIONING

(76) Inventors: Naum Klinberg, 350 Dutchman's La., Apt. 1009, Louisville, KY (US) 40205; John B. Carroll, 2804 Springbud Ct., Louisville, KY (US) 40220

( * ) Notice: Subject to any disclaimer, the term of this patent is extended or adjusted under 35 U.S.C. 154(b) by 147 days.

(21) Appl. No.: 09/938,847

(22) Filed: Aug. 24, 2001

(65) Prior Publication Data

US 2003/0037789 A1 Feb. 27, 2003

(51) Int. Cl.⁷ .............................................. A61M 16/00
(52) U.S. Cl. ........................ 128/207.14; 128/207.15
(58) Field of Search .................. 128/200.24, 200.26, 128/207.14, 207.15, 207.16, 207.17, 207.18, 911, 912, 206.26; 604/93.01, 96.01, 98.01, 102.01, 118, 119, 128

(56) References Cited

U.S. PATENT DOCUMENTS

| | | | |
|---|---|---|---|
| 4,240,417 A | | 12/1980 | Holever |
| 4,280,500 A | * | 7/1981 | Ono .............................. 604/523 |
| 4,510,933 A | | 4/1985 | Wendt et al. |
| 4,627,433 A | * | 12/1986 | Lieberman ............. 128/207.16 |
| 4,669,463 A | * | 6/1987 | McConnell ............ 128/207.14 |
| 4,674,495 A | * | 6/1987 | Orr ....................... 128/207.14 |
| 4,723,543 A | | 2/1988 | Beran |
| 4,836,199 A | * | 6/1989 | Palmer .................. 128/207.16 |
| 5,054,482 A | | 10/1991 | Bales |
| 5,062,420 A | * | 11/1991 | Levine .................. 128/204.18 |
| 5,259,376 A | | 11/1993 | Bales |
| 5,282,463 A | | 2/1994 | Hammersley |
| 5,287,852 A | | 2/1994 | Arkinstall |
| 5,458,139 A | | 10/1995 | Pearl |
| 5,664,564 A | | 9/1997 | Palmer |
| 5,694,922 A | * | 12/1997 | Palmer .................. 128/202.27 |
| 5,771,888 A | * | 6/1998 | Keim ..................... 128/207.15 |
| 5,832,920 A | * | 11/1998 | Field ...................... 128/207.14 |
| 5,964,217 A | | 10/1999 | Christopher |
| 6,047,699 A | | 4/2000 | Ryatt et al. |
| 6,135,111 A | * | 10/2000 | Mongeon ............... 128/207.15 |
| 6,513,527 B1 | * | 2/2003 | Abdel-Aziz ............ 128/207.14 |
| 6,575,166 B2 | * | 6/2003 | Boussignac ............ 128/207.14 |
| 2001/0044600 A1 | * | 11/2001 | Elkins ........................ 604/119 |

* cited by examiner

Primary Examiner—Aaron J. Lewis
Assistant Examiner—Teena Mitchell
(74) Attorney, Agent, or Firm—David W. Carrithers; Carrithers Law Office, PLLC (57) ABSTRACT

A measured suction system utilizes a tracheostomy tube apparatus includes a tracheostomy tube, Tracheostomy collar, and swivel adapter. The tracheotomy tube includes an internal channel within the Tracheostomy tube allowing for all suctioning of the patient. The system will insure that all negative suction pressure is maintained within the Tracheostomy tube, which eliminates any trauma that may be caused by using excessive negative suction pressures when the standard methods of suctioning are employed. The new system also reduces the risk of infection caused by using the sterile invasive suction techniques.

13 Claims, 14 Drawing Sheets

TRACHEOSTOMY TUBE APPARATUS FOR NONINVASIVE SUCTIONING

BACKGROUND OF THE INVENTION

1. Technical Field

This Tracheostomy tube system provides a Tracheostomy tube, Tracheostomy collar, and swivel adapter for measured suctioning of the patient in a non-invasive manner and at a controlled negative suction pressure.

2. Description of the Related Art

A Tracheostomy is an opening through the neck into the trachea through which an indwelling tube may be inserted. An incision is made into the trachea through the neck below the larynx. The opening may be made as an emergency measure or performed as scheduled in an operating room. The incision is made through the skin through the second, third, or fourth tracheal ring. A small hole is made in the fibrous tissue of the trachea, and the opening is then dilated to allow the intake of air.

Airway problems that may require the performance of a Tracheostomy could include tumors, such as cystic hygroma; laryngectomy; infection, such as epiglottitis or croup; subglottic stenosis; subglottic web; tracheomalacia; vocal cord paralysis (VCP); laryngeal injury or spasms; congenital abnormalities of the airway; large tongue or small jaw that blocks airway; Treacher Collins and Pierre Robin Syndromes; severe neck or mouth injuries; airway burns from inhalation of corrosive material, smoke, or steam; obstructive sleep apnea, and foreign body obstruction. In addition, lung conditions that could require a Tracheostomy include a need for prolonged respiratory support, such as Broncho pulmonary Dysplasia (BSD); chronic pulmonary disease to reduce anatomic dead space; chest wall injury; or diaphragm dysfunction. Other conditions include neuromuscular diseases that cause paralysis or weakening of the chest muscles and diaphragm, fracture of the cervical vertebrae with spinal cord injury, long-term unconsciousness or coma, disorders of respiratory control such as congenital central hypoventilation or central apnea, and facial surgery of facial burns.

After undergoing a Tracheostomy procedure because of respiratory disorders, individuals require the use of a Tracheostomy tube assembly connected to a mechanical ventilator to assist their breathing. Today there are three basic indications for a Tracheostomy in a pediatric patient: upper airway obstruction, assisted ventilation, and pulmonary toilet.

There are several different types of Tracheostomy tubes available. The ideal tube should be soft, pliable, easy to clean and maintain, and available in a variety of sizes and lengths. The choice of type and size of tube should be based on the indication for the procedure.

U.S. Pat. No. 4,510,933 by Wendt et al teaches a suction adapter and medical draining set and method of using a tracheal draining device wherein the suction adapter is attached directly to the Tracheostomy tube and facilitates suctioning with a suction catheter which allows a opening to advance the catheter through this device to be introduced into the patent's lower airway and is now considered against the American Thoracic Society (ATS) recommendations. The above mentioned U.S. Pat. No. 4,510,933 does not eliminate the possibility of infection caused by deep suctioning or the trauma that is associated with it.

As set forth in U.S. Pat. No. 4,240,517 by Holever, a tracheal tube adapter is connected to the end of the Tracheostomy tube and is designed to facilitate deep suctioning which is against the ATS recommendation. The device does not eliminate any of the problems typically associated with deep suctioning.

The device taught in U.S. Pat. No. 5,664,564 by Palmer teaches an aspirating and ventilating device to allow deep suctioning through the use of a catheter that is stored inside of a sterile baggy and can be reused for up to twenty-four hours. Again, its intended purpose is for deep suctioning which is against the ATS recommendation. Although this patent has decreased the cost of deep suctioning by reducing the number of catheters that have to be used to maintain a patent's airway, it has not eliminated all the contra indications associated with deep suctioning. By maintaining a catheter inside the sterile bag, it has reduced the risk of infection associated with poor techniques by the care giver which allows infection to be introduced into the patients lungs. However, it does not eliminate the complications associated with tracheal damage caused by the pointed suction catheters that are utilized with these types of systems, or the damage that can be done from using excessive pressures.

This particular patient is U.S. Pat. No. 4,723,543 by Beran teaches an endotracheal tube connecting to the outside of the Tracheostomy tube and inside the patient Y adapter. Its only function is to measure pressure or gas sampling as a pneumatic that will measure the patient's respiratory flow rate.

U.S. Pat. No. 5,282,463 by Hammersley and U.S. Pat. No. 6,047,699 by Ryatt et al teach anti-disconnect device designed to secure the trach to the circuit.

U.S. Pat. No. 5,287,852 by Arkinstall teaches an apparatus and method for maintaining a tracheal stoma. This particular system is not designed to provide ventilation or secretion management.

This U.S. Pat. No. 5,964,217 by Christopher teaches a tube for insertion into the patient's nose or mouth in emergency situations; not for long term management of a patient's airway, like a Tracheostomy tube. These type of tubes are used for short periods of times of approximately two weeks or less, to provide a patent airway in emergency situations.

The Tracheostomy tube, ("trach"), must be suctioned several times per day. The purpose of Tracheostomy suctioning is to remove mucus from the trach or windpipe. The procedure is performed with sterile equipment. Before and after the procedure, the patient may receive oxygen to reduce the risk of hypoxemia. The suction is applied for no more than 10 to 15 seconds at a time and should be discontinued if the patient experiences respiratory distress. The catheter used for suctioning should be no larger than one-half the diameter of the Tracheostomy tube.

SUMMARY

The present invention provides for a new tracheostomy tube to be used with various types of trach apparatus for completing the suctioning procedure. The embodiments use the new tracheostomy tube that allows suctioning to be done using a non-invasive method. One embodiment is used in conjunction with a modified tracheostomy collar that incorporates the suctioning mechanism therein or modified swivel adapter that incorporates a suctioning mechanism. Whether or not the patient requires mechanical ventilation will determine when to use the tracheostomy collar verses the swivel adapter. The other alternative is to use the new tracheostomy tube in conjunction with the standard trach collars and swivel adapters that are on the market today.

Conventional Tracheostomy tube designs require that the Tracheostomy tube be inserted into the patient's throat by an invasive techinque using a pointed tip such as is currently available with a pointed tip suction cather. These conventional suction catheters feature a sharp, pointed tip at the far end. During insertion and removal, the sharp tip can cause discomfort. In addition, the respiratory mucosa can be injured, torn, or otherwise damaged due to the sharp tip and the procedure wherein the catheter is introduced or remove from the Tracheostomy tube. Reducing the trauma associated with the use of pointed tips and/or deep suctioning reduces the likelihood or the propensity for further medical complications. Moreover, conventional suctioning methods cause increased tracheal damage and infection, which often require tracheal surgery, particularly in the pediatric population.

The instant invention offers a non-invasive alternative to the standard products and procedures. The present invention features a swivel adapter with a built-in suction tubing connection for use on the ventilated patient. The modified component utilizes a standard fitting.

The instant product design complies with the American Thoracic Society's recommendation for suctioning using the "Measured Suctioning Technique". The technique involves suctioning the length of the trach tube and no further. The inventors believe the use of a non-invasive technique combined with this modified equipment would reduce discomfort or trauma to the patient, thereby reducing the risk of complications.

For children, making the procedure less uncomfortable would make the child more cooperative. This could enable the procedure to be performed in a timelier manner and with less distress. Further, the procedure could be performed with greater efficiency and reduced risk of injury. This would result in less complications, including infection.

It is an object of the present invention to provide a suction system utilizing a noninvasive technique to reduce the many risks and complications associated with deep suctioning.

It is an object of the present invention to provide a means for noninvasive suctioning which greatly reduces the opportunity of infection.

It is an object of the present invention to provide a device and the methodology which complies with the American Thoracic Society recommendation for suctioning using measured suctioning techinque.

It is an object of the present invention to provide a device, with reduced trauma and risk of infection, thereby potentially reducing the risk of hypoxemia, dysrhythmia, bleeding, infection, atelectasis, hypotension, and bradycardia.

It is an object of the present invention to provide a device, that reduces discomfort through a non-invasive technique.

It is an object of the present invention to provide a device, that not only complies with the American thoracic Society recommendation by eliminating the need for deep suctioning the patient but will allow suctioning using a non-invasive method.

Using the new trachestomy tube with he modified tracheostomy collar and swivel adapter is simple. When working with a patient that is not on mechanical ventilation, the modified tracheostomy collar would be used. The collar is placed directly over the tracheostomy opening and is secured with a cord about the neck. A small lumen tube built inside the trach collar connects the trach tube and trach collar together. The suction port located at the base of the trach collar connects to a dual press button adapter for aspiration from the trach mask and/or trach tube. The suction port is then connected to a collection canister which is connected to the vacuum tubing extending from the vacuum source.

When working with a patient on mechanical ventilation the modified swivel adapter is used instead of the modified trach collar. The modified swivel adapter is snapped over the treasotomy tube, and the other end of the swivel adapter is connected to the patient circuit. The suction tubing adapter from the collection canister is connected to the vacuum tubing extending from the vacuum source.

An alternate method using the present invention of the new tracheostomy tube is used independent of the modified trach collar and modified swivel adapter. It may be used with the current trach collars and swivel adapters already on the market.

It provides a short lumen tube that accessed the suctioning channel at the base of the trach head. The lumen tube has a press button adapter to allow suction pressure to be directed to the trach tube base. In addition, it has a barbed end to allow for connection to standard suction tubing.

BRIEF DESCRIPTION OF THE DRAWINGS

A better understanding of the present invention will be had upon reference to the following description in conjunction with the accompanying drawings in which like numerals refer to like parts throughout the several views and wherein.

DESCRIPTION OF THE PREFERRED EMBODIMENTS

In reference to the drawings, the instant invention consists of the novel Tracheostomy tube device 10 including a trach tube 11 having a first primary conduit 12 with a built-in partition wall 14 forming a secondary tube channel 16 preferably integral therewith to allow suctioning to the base of the tube 11 using a non-invasive technique. Moreover, the tube 10 can be utilized in combination including a modified trach collar 18, (sometimes referred to as a mask) with a built-in dual press button suction adapter. It also has the lumen tubing for insertion to the trach tube head 17 at an enlarged portion forming a collar 23. A small dual press button adapter 74 allows suctioning of either the head 17 of the trach tube 11, the lower portion 32 of the trach collar 18, or both simultaneously. Also adaptable to the instant invention is a single press button swivel adapter 22 with built-in suction tubing adaptor (barbed outlet) 24 and tubing 26 for insertion to the trach secondary tube channel 16. This application is used for patients receiving mechanical ventilation. The system offers patients who have the ability to access and use the dual press button adapter to self-suction without the need of a care giver. This system also accommodates both ventilator and non-ventilator patients. The assembly can be used for all patients who have a tracheostomy.

Figure 1:
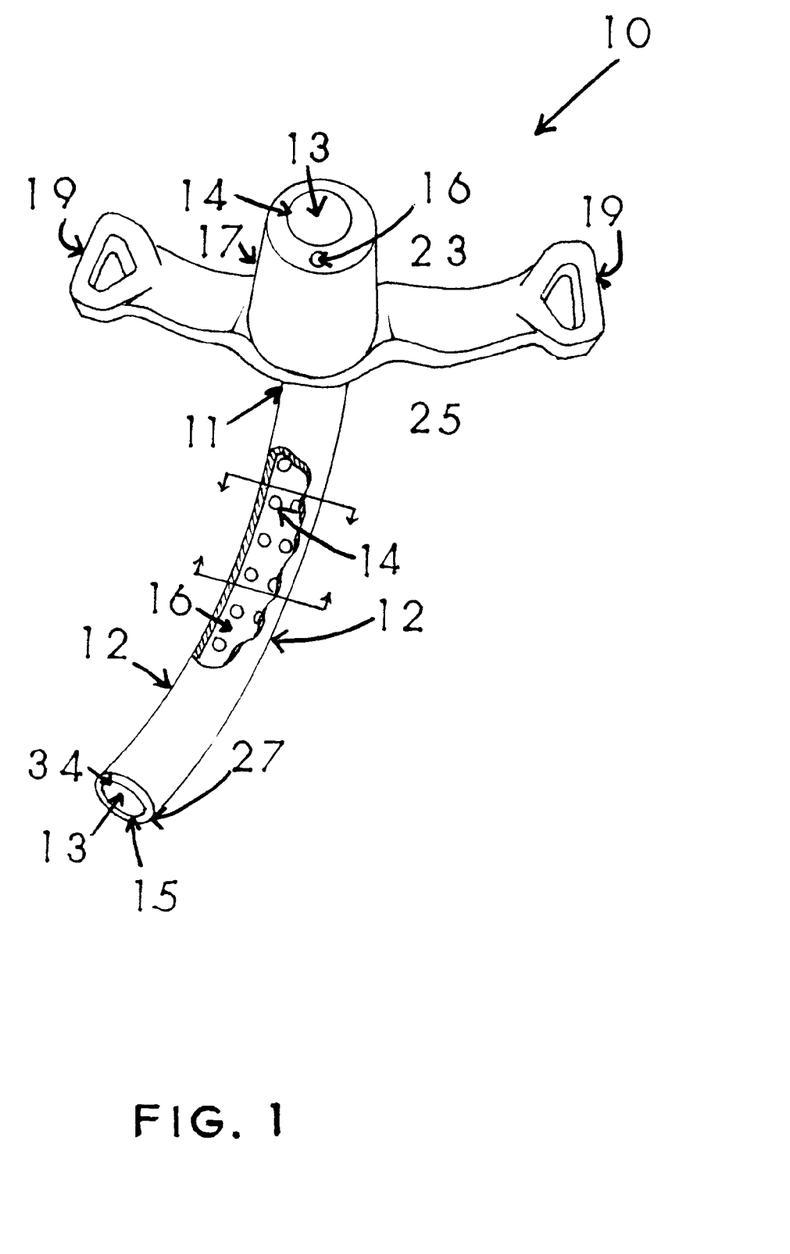
FIG. 1 is a front oblique cutaway view of the present invention showing a Tracheostomy tube assembly for use with vacuum attachments including a pair of parallel channels extending along a portion of the bottom of the tube to the trach head including an air flow channel and a barrier permitting fluid exchange (such as a porous membrane or preferably a strip of material having holes therein which maintains its structural integrity and resists deformation during a suctioning process), extending axially therethrough in fluid communication with and showing alternate vacuum attachment points.
Figure 2:
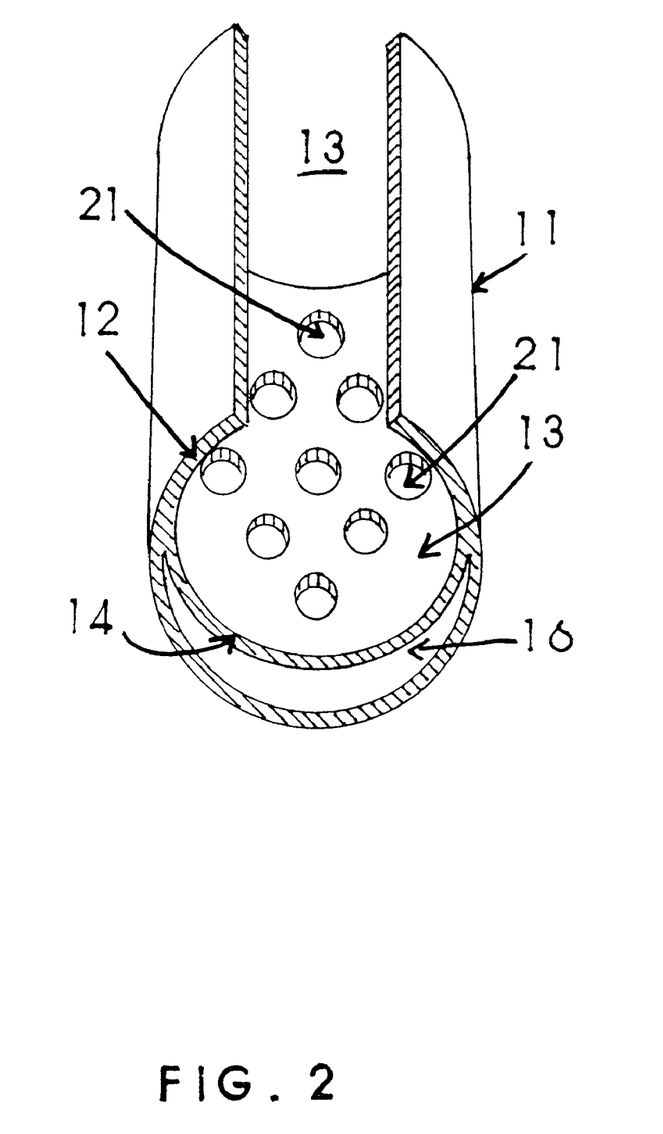
FIG. 2 is a partial cutaway prospective view showing the trach tube defined as a circular outer tube wherein a selected portion thereof includes a partition means separating the interior of the tube into two flow passages, wherein the separating means contains at least one and preferably a plurality of perforations or holes therethrough allowing passage of fluid from one passage to the other.
Figure 10:
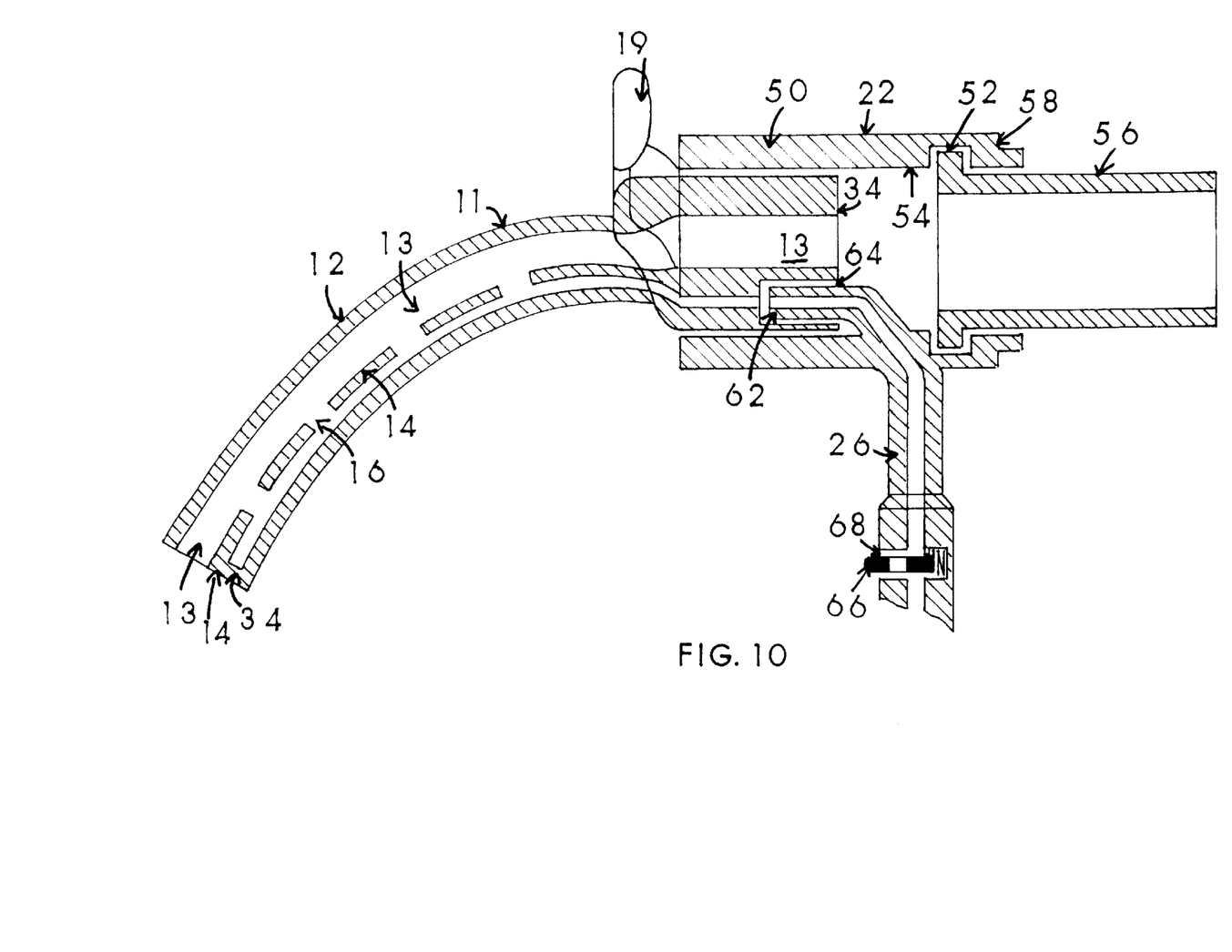
FIG. 10 is a cross-sectional view of the present invention showing a swivel adapter and modified trach tube in cooperative engagement including the press button adapter to facilitate suctioning of fluid from the base of the trach and used in conjunction with mechanical ventilation.
Figure 11:
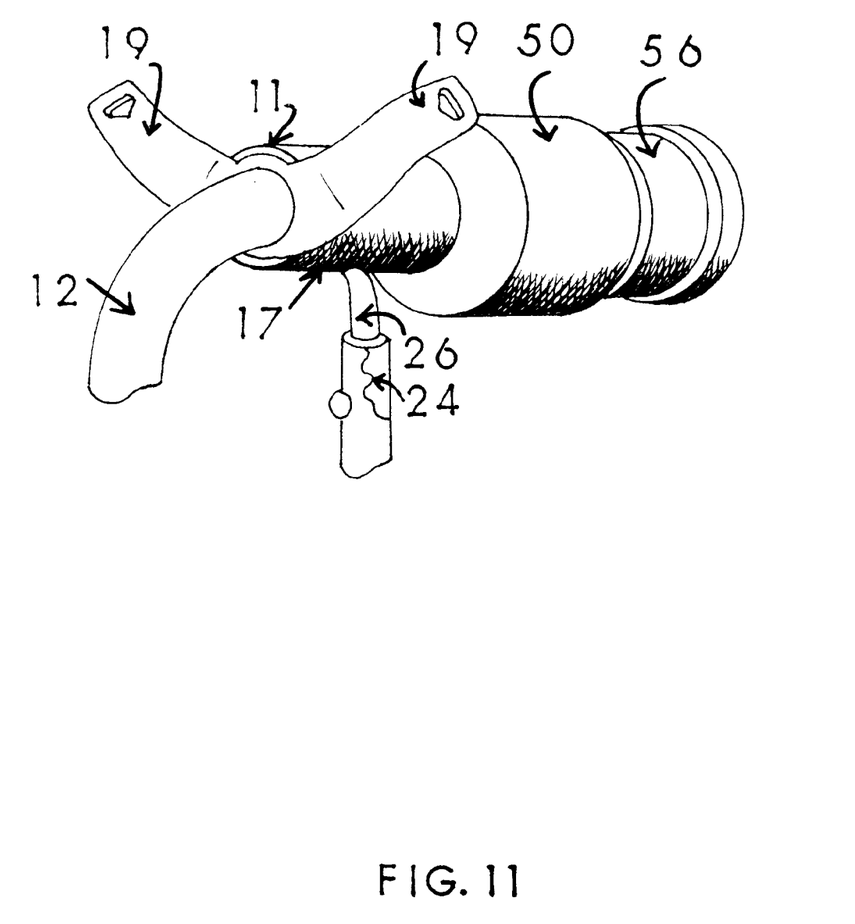
FIG. 11 is a perspective view of FIG. 10 showing the swivel adapter.
Figure 12:
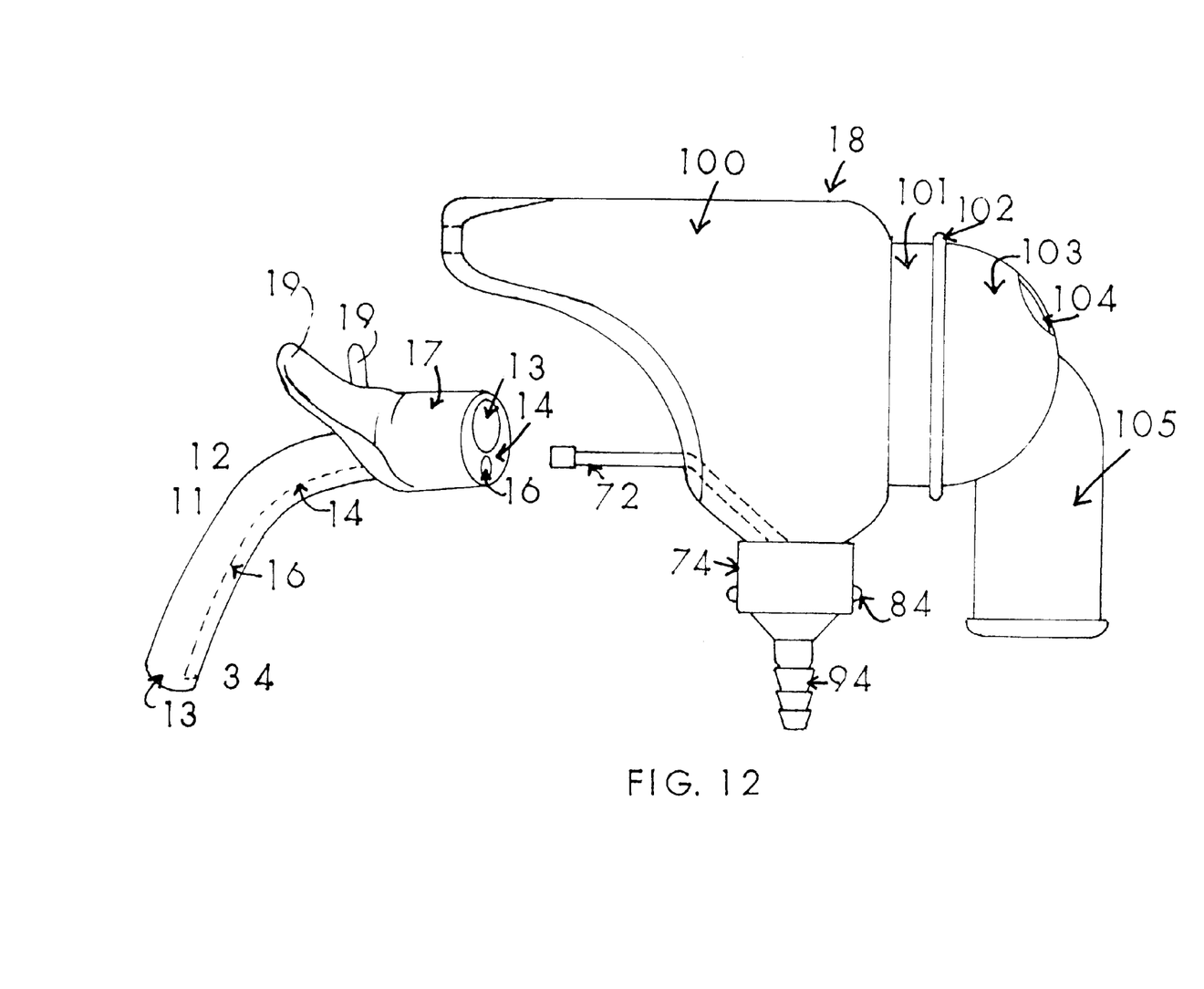
FIG. 12 is a perspective lateral view of the present invention showing a modified trach collar having a dual press button adapter to facilitate suctioning of fluid from the collection base of the modified trach collar and/or suctioning fluid through the channel and tube.

As shown in FIG. 1, a new tracheostomy tube assembly for use with vacuum attachments includes a pair of generally parallel conduit channels sharing a common sidewall extending along a portion of the bottom of the tube separated by a partition wall which permits the exchange of fluids therethrough and extends to the trach head defining an air flow channel and a fluid channel in fluid communication with one another. More particularly, the Tracheostomy tube 11 includes a primary or first tube or conduit defining a stem 12 having an opening or flow passage defining a first channel 13 extending from a distal end 15 therethrough to the top portion defining a head 17 of the trach 11 that extends past a pair of side flanges 19 and into the stem of the Tracheostomy tube. One or more plugs 25 may be formed or removably held in the head 17 for attachment of tubing. The stem 12 of the trach 11 extends into the patient's trachea. The stem 12 is a generally cylindrical elongated tube. The base of the stem 12 defining the distal end 15 has an inner fold that has multiple small openings in it which may be slits, slots, or other apertures of a selected number and size to provide a selected area. More particularly, the trach tube 11 defines a first air passage tube encircling a smaller suction tube forming parallel flow passages. The trach tube 11 may also be defined as a circular outer tube wherein a selected portion thereof includes a means for separation defining a wall, film, or membrane or other fluid separation barrier separating the interior of the tube into two flow passages, wherein the separation barrier contains at least one and preferably a plurality of perforations or holes therethrough allowing passage of fluid from one passage to the other as best shown in FIGS. 1, 2, and 10. Thus, the preferred embodiment is a tube having a partition wall 14 with openings 21 therein separating the first fluid flow passage channel 13 from the second fluid flow passage 16. In the preferred embodiment the larger first channel 13 is separated by a smaller second channel 16 by a partition 14 which extends from the distal end 15 of the stem 12 upward for a selected distance preferably to the head 17, but which may extend into the head 17 of the trach 11. The secondary channel 16 is sealed over at the end by a plug or the molding process forming a means for sealing 34 to promote suction of fluids from the primary channel 13 thorough the holes or openings 21. It is also contemplated that a flat, semicircular, or arcuate longitudinal strip having openings 21 therein may be inserted into a tube forming the dual flow passage arrangement. An obturator may be fitted to the distal end 15 of the base 27 to facilitate entry of the stem 12 into the patient's trachea.

Use of the novel trach tube 11 attached to suction tubing to the opening in the trach head 17, will direct negative suction pressure into the stem of the Tracheostomy tube. The negative suction pressure will then be directed to the holes on the posterior portion of the Tracheostomy tube; thereby clearing any fluids that are inside the Tracheostomy tube. At the base of the stem 12, the inner fold or partition wall is closed off; thereby insuring that all suction pressure is maintained within the Tracheostomy tube 11 which eliminates any trauma that may be caused by using excessive pressures.

Figure 3:
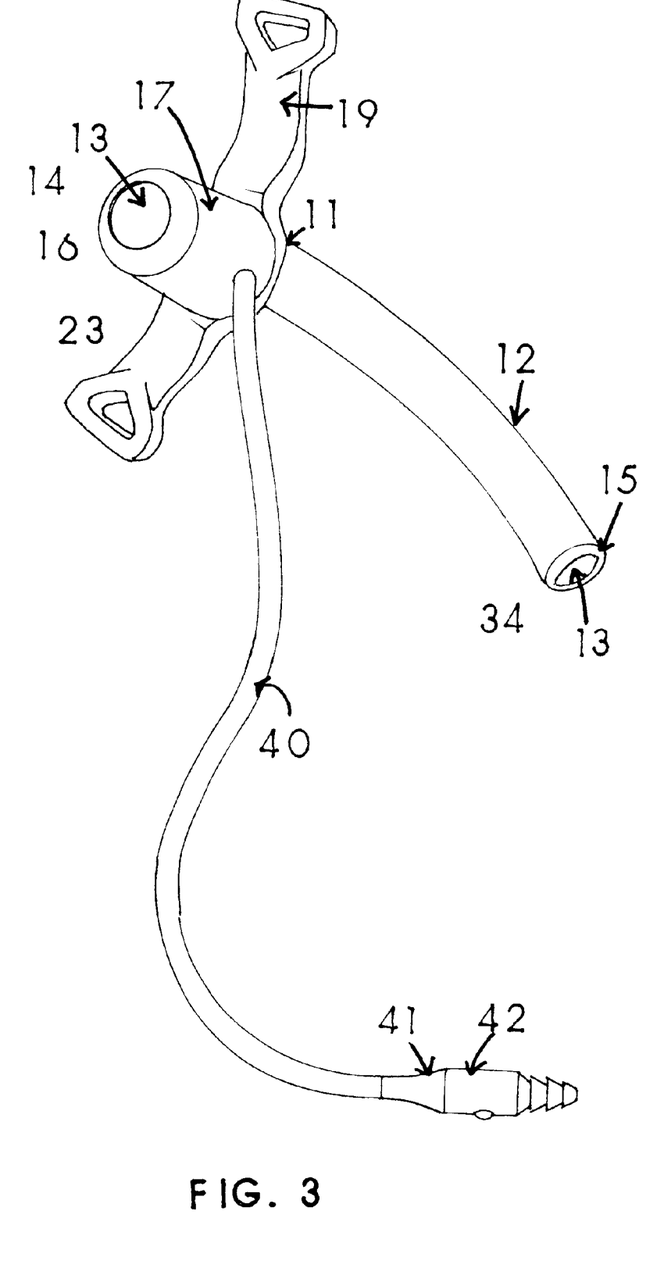
FIG. 3 is a perspective view of the present invention showing a hand controlled suction line adapter for use with children and/or infants.

FIG. 3 is a perspective side view of the trach tube 11 showing a hand controlled suction line hand adapter 41 for use with children and/or infants including a single push button actuator 42 to open or close the suction passageway of the tube in order to control the suction pressure.

Figure 4:
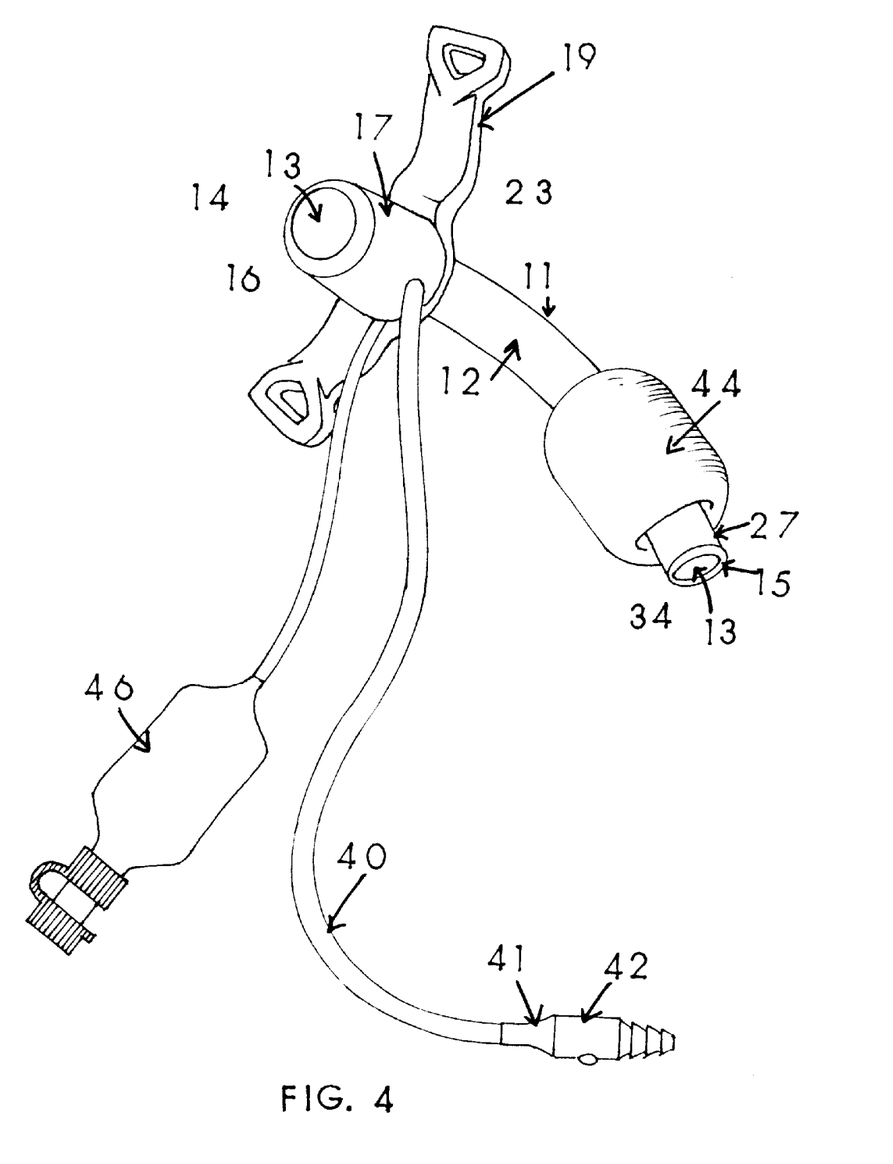
FIG. 4 is a perspective view of the invention of FIG. 3 for use with adults including a trach cuff and pilot balloon.

As shown in FIG. 4, the trach tube 11 shows a suction line 40 connected to a hand actuated adapter assembly 41 for use with adults including a single push button actuator 42 to open or close the suction passageway of the tube in order to control the suction. Also shown is a trach cuff 44 to insure a proper seal when using mechanical ventilation and a pilot balloon 46 for use to expand the cuff.

Figure 5:
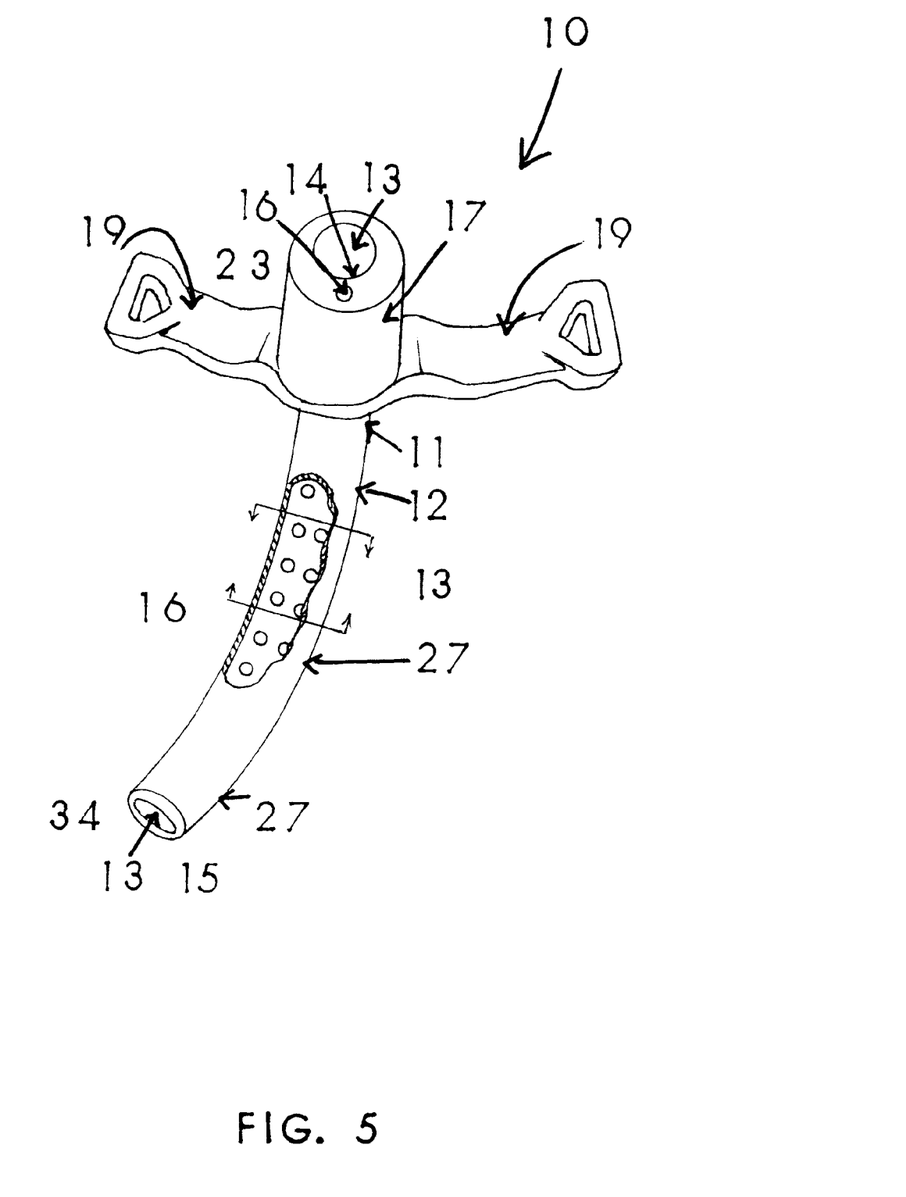
FIG. 5 is a perspective view of a Tracheostomy tube assembly showing a head having a fluid connection channel for suction in the head of the trach for cooperative engaging with a modified trach collar or modified swivel adapter for mechanical ventilation for use with pediatric or infant patients.
Figure 6:
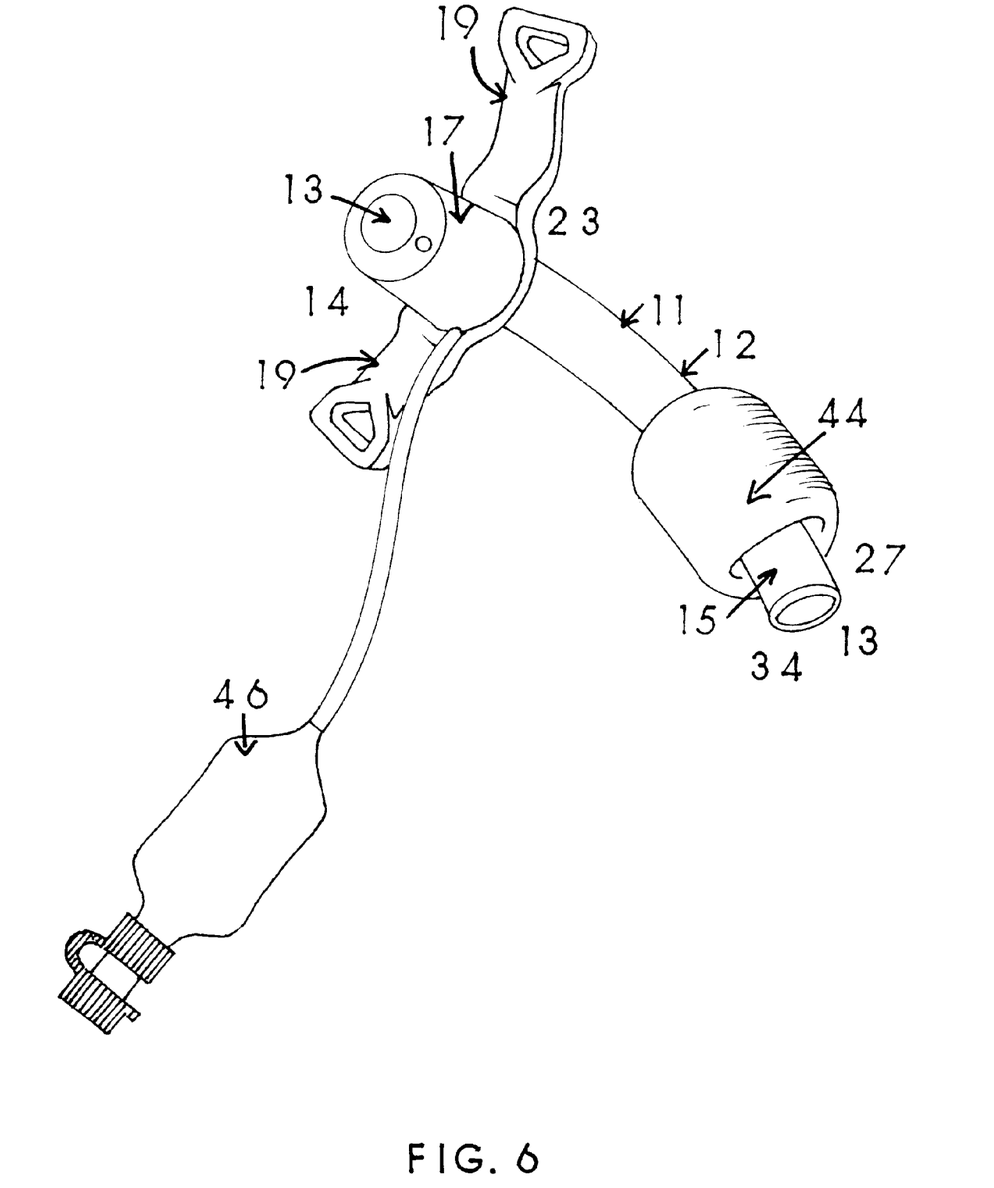
FIG. 6 is a perspective view of the Tracheostomy assembly of FIG. 5 including a trach cuff and pilot balloon for use with adult patients.
Figure 7:
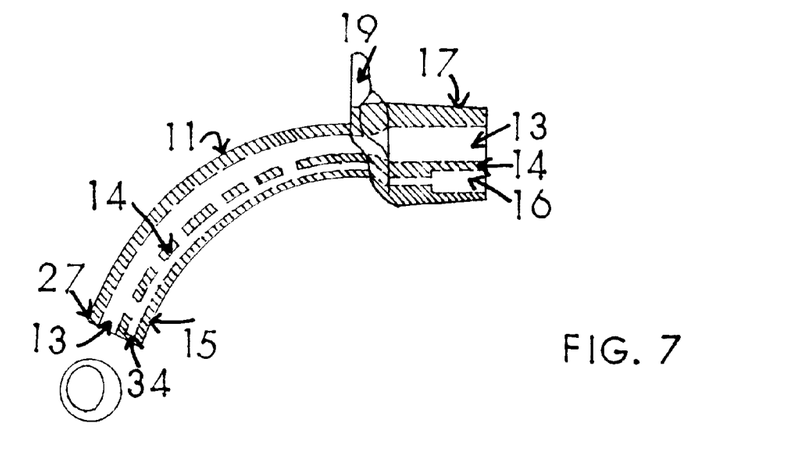
FIG. 7 is a partial sectional view of the trach tube assembly showing the channel extending through the head of the trach tube as shown in FIG. 5.
Figure 8:
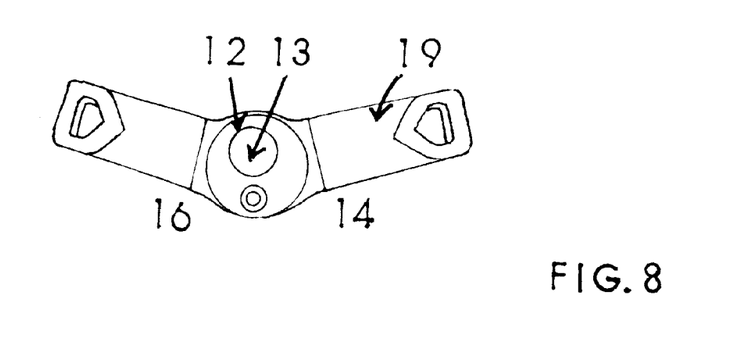
FIG. 8 is a front view showing the flanges extending laterally from the head of the trach tube and the channel penetrating the trach head.

The tracheostomy tube assembly shown in FIG. 5 includes a head 17 having a fluid connection channel in the head of the trach for cooperative engaging with a trach collar 18 or swivel adapter 22 for mechanical ventilation for use with pediatric or infant patients. FIG. 6 shows the Tracheostomy assembly of FIG. 5 including a trach cuff 44 and pilot balloon 46 for use with adult patients. As illustrated in FIGS. 7 and 8, the trach tube assembly is shown in a cross-sectional view showing the channels 13, 16 extending through the head 17 of the trach tube 11.

Figure 9:
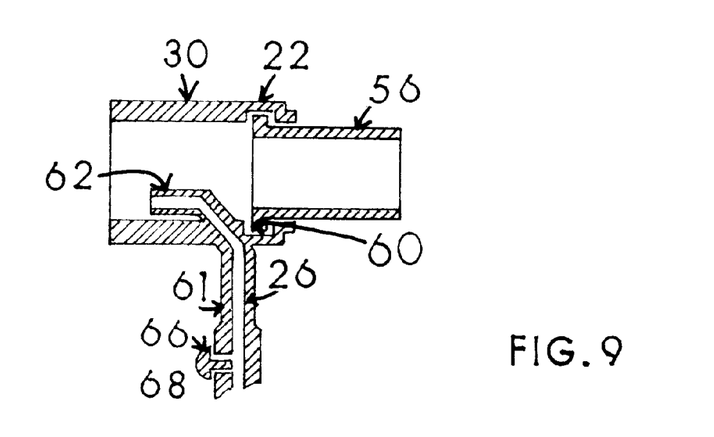
FIG. 9 is a cross-sectional view of a swivel adapter.

As shown best in FIGS. 9 and 10, a swivel adapter 22 with a built in suction tubing adapter includes tubing for cooperative engagement with the Tracheostomy tube and a press button adapter to facilitate suctioning of fluid from the base of the trach and used in conjunction with mechanical ventilation. The swivel adapter 22 is similar to the conventional swivel adapters. The modified swivel adapter 22 of the present invention has two separate pieces that are allowed to turn independently of each other which is for added patient comfort. The swivel adapter 22 includes a first cylindrical tube 50 having a internal diameter sized and shaped to cooperatively engage the outer diameter of the trach tube head 17 when inserted therein. A groove 52 of greater diameter is formed within the inner surface 54 of the first cylindrical tube 50. A second cylindrical tube 56 having a smaller exterior diameter coaxially and rotatably engages the interior surface of the first diameter tube 50 at a distal end 58 opposing the trach head 17. The second cylindrical tube 56 includes a flange 60 extending around the periphery of the exterior surface for cooperative rotational engagement with the groove 52 of the first cylindrical tube 50. Additional tubing may be connected to the second cylindrical tube 56.

The novel press button swivel adapter 22 of the instant invention includes an suction adapter 61 and an internal suction connection 62 that is designed to be directly inserted into and cooperatively sealingly engage a corresponding opening or socket 64 of the Tracheostomy tube head 17. The internal suction connection 62 may be formed as by molding in a one piece unit with the swivel adapter 22, or an opening in the swivel adapter may accommodate a suction connection 62 protruding therethrough.

At the posterior portion of the suction connection 62, a single press button 66 having a plunger, such as a spring loaded plunger, is cooperatively fitted to a connection point including a bore 68 in fluid communication with a vacuum/suction which is to activate and direct suction pressure into the suction adapter which is created in the internal suction connection 62 by a vacuum source, whereby suction can then redirected into the head of the Tracheostomy tube 17 and then into the Tracheostomy tube stem 12. This easy to use press button swivel adapter 22 provides patients with the ability to self-suction as needed and reduce the need for a care giver.

A modified trachestomy collar 18 may be used with the trach tube 10 of the instant invention with patients that are not receiving mechanical ventilation, but that are on oxygen and/or humidity setups.

Figure 13:
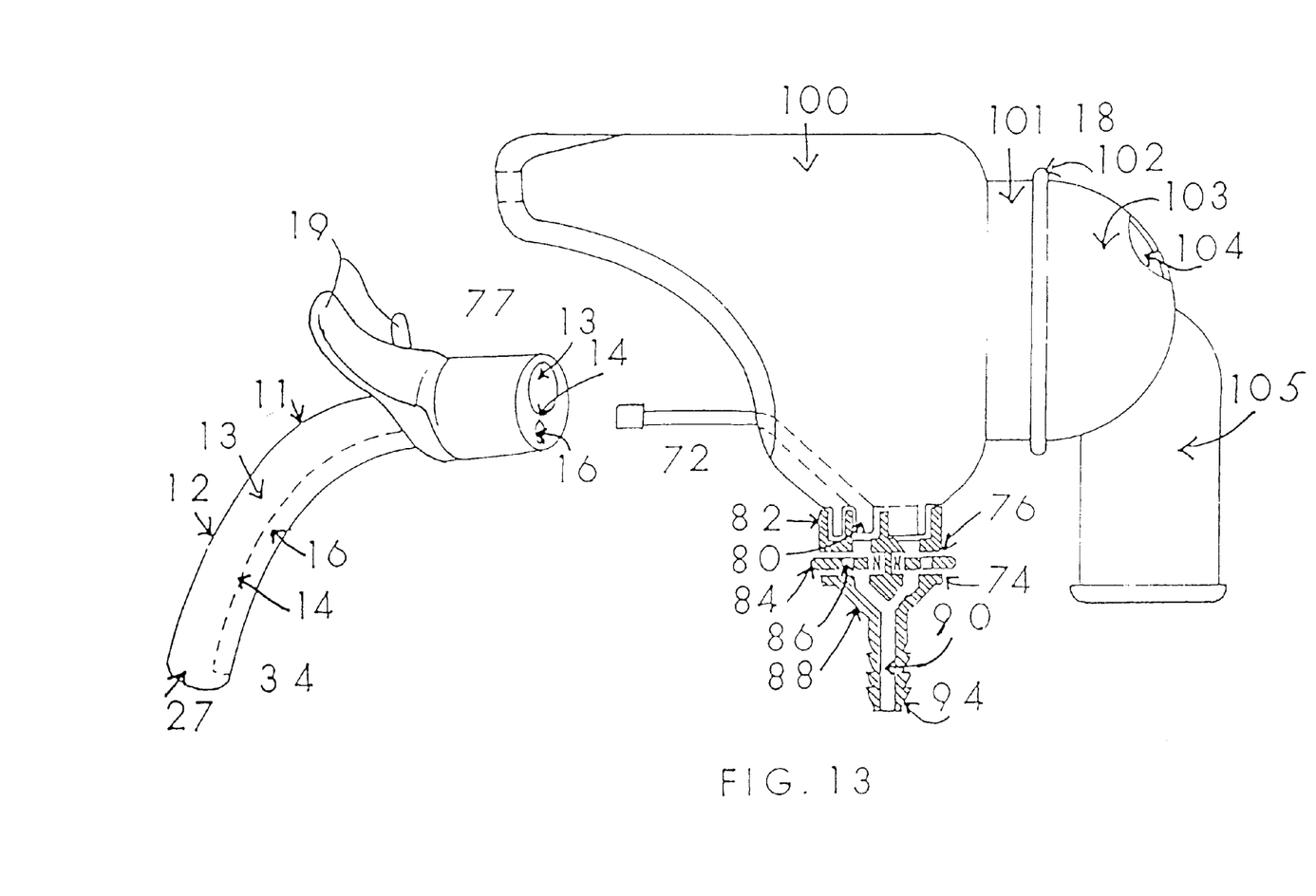
FIG. 13 is a partial perspective lateral view of the modified collar and trach tube assembly of FIG. 12 showing a sectional view of the dual press button adapter.
Figure 14:
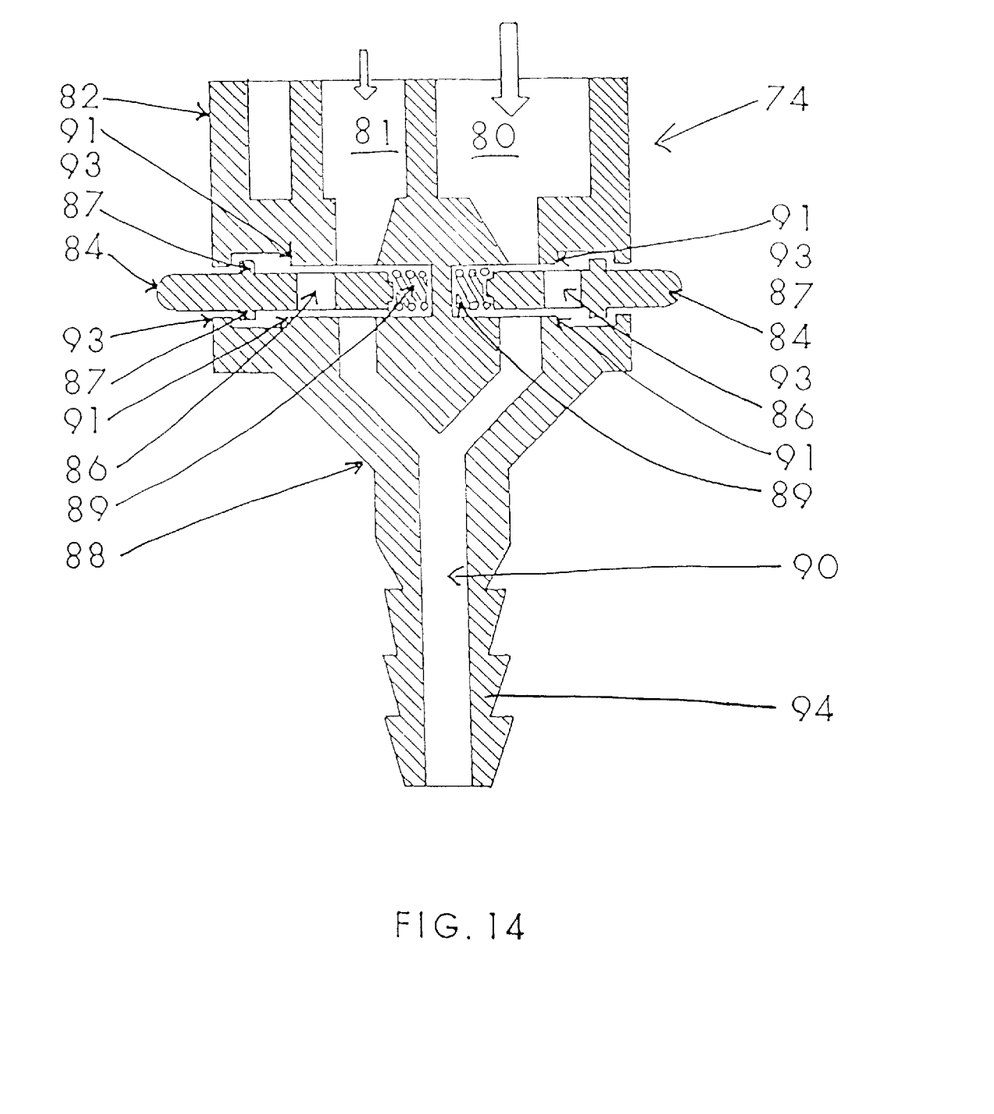
FIG. 14 is an enlarged sectional view of the dual press button adapter of FIG. 13.
Figure 15:
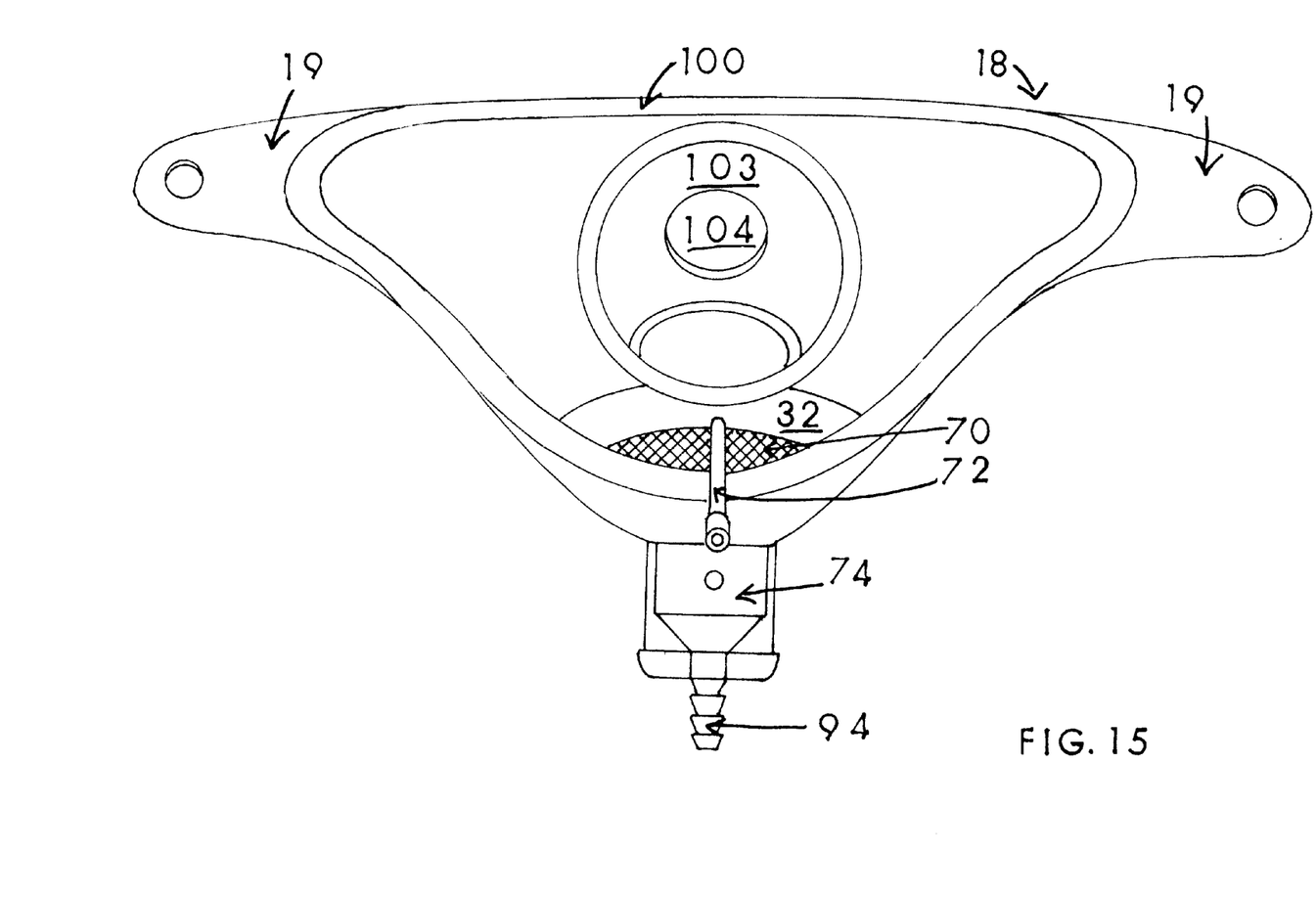
FIG. 15 is a rear perspective view of the modified trach collar showing an interior view of the base trap with screen suction port collector, dual press button adapter and large bore tubing connector.

As shown in FIGS. 12–16, the trach collar 18 has the appearance of a conventional tracheostomy collar comprising a mask 100 including a large cylindrical bore 101 swivelly connected at a flange 102 to a hemispherical shaped air mixing chamber 103 having an air opening therein and a large bore tubing connector 104 extending therefrom. Improvements have been made at the posterior portion of the collar 18 where a means for gathering with a screen like device 70 is inserted in the lower portion thereof and a small lumen tube 72 in close proximity thereto extends therefrom for insertion to the trach tube channel 16. Preferably a two-button press button adapter 74 is attached to the bottom of the collar having means for actuating defining a spring and plunger assembly 76 providing the user with means for suctioning of either the trach tube 11 or the base of the trach collar 18. As best shown in FIGS. 13 and 14, the adapter 74 includes two channels, a first channel 80 connecting to the mask transferring fluid coming from an opening in the base of the trach tube channel or airway 13 of the trach tube 11, and a second channel 81 connecting to an distal end of a small lumen tube 72 of the trach collar transferring fluid from the bore 16 of the trach collar 11, both connecting to a common suction channel 90 extending downward from cylindrical body 82. A pair of plungers 84, shown in the closed position, having openings 86 therein are spring loaded and positional for cooperative alignment with the channels 80 of the adapter upon depression either together or independently to provide a means for suction to be applied through a selected one or both channels to clear the base of the collar 18, trach tube 11, or both. As shown in FIG. 14, a pair of opposing springs 89 are biased inwardly by pressing the buttons 84 permitting sliding movement of the plungers 84 to a preselected position limited by a pair of flanges 87 cooperatively engaging corresponding spaced apart shoulders 91 and 93 respectively. A tip 88 connects channels 80 and 81 converges into a common channel 90 alignable to the openings of the openings 86 and channels 80, 81 of the body extends from the bottom of the cylindrical body 82 extending to a single line having a barbed outer surface forming an nipple outlet 94 for connecting to a vacuum line.

Figure 16:
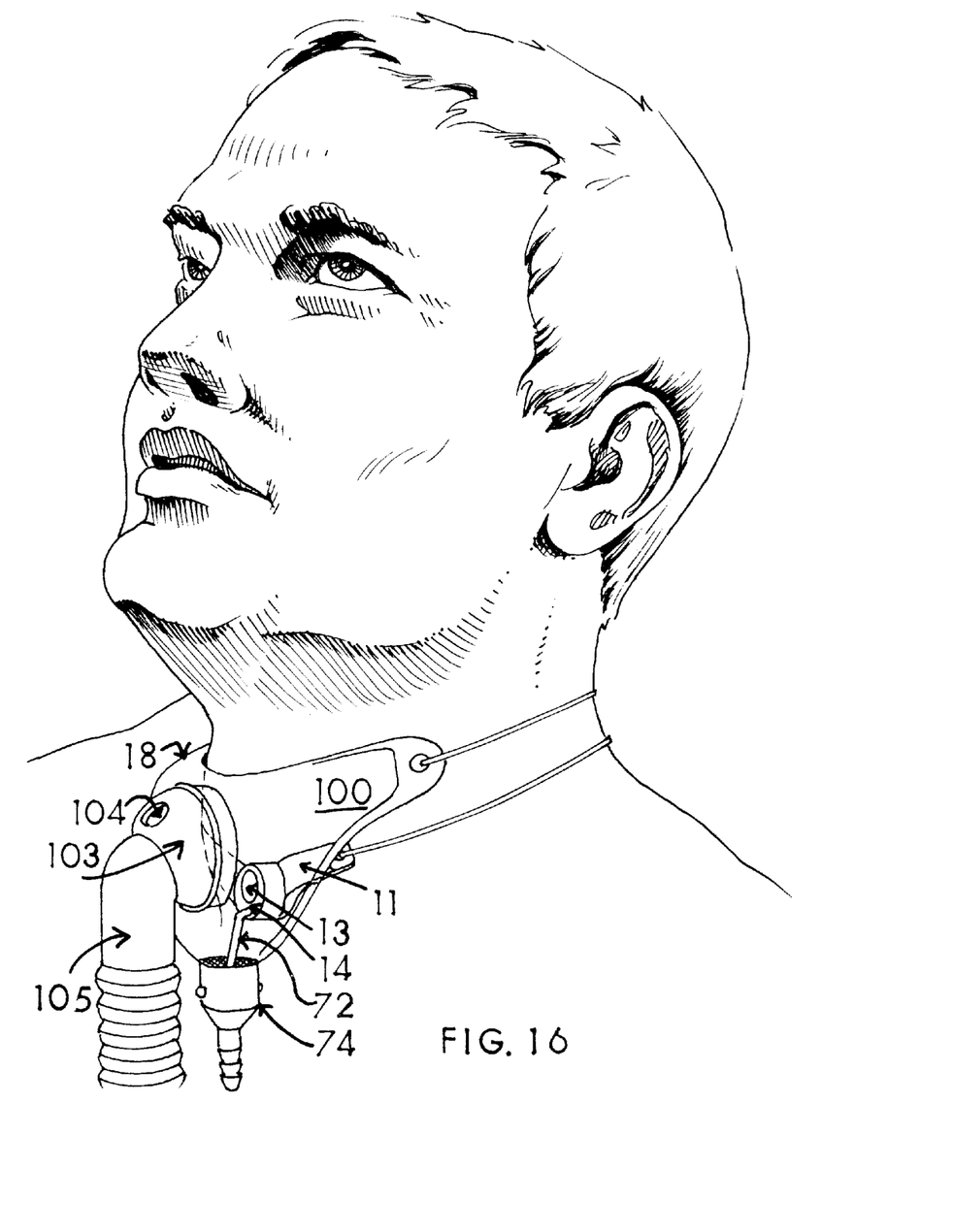
FIG. 16 is a perspective view of the modified trach tube, modified trach collar, and dual press button adapter of FIGS. 5 and 15 mounted to the patient.

As shown in FIG. 16, once the Tracheostomy collar 18 is in place with the elastic strap fastened around the patient's neck, the small lumen tubing 72 that has been built into the tracheostomy collar 18 will then be inserted into the opening of the Tracheostomy tube head 17. Suction tubing is added to the two-button adapter 82 that has been connected to the Tracheostomy collar 18. Wall suction pressure in the "ON" position will then be directed to the two-button adapter 82. Pressing the button would direct the negative suction pressure into the small lumen tubing 72 which would redirect the pressure into the tracheostomy tube head 17. By pressing the other button, the pressure will be redirected into the posterior portion of the Tracheostomy collar 18 where secretions tend to settle as patients tend to cough into the Tracheostomy collar. If both buttons are pushed simultaneously, then negative suction pressure could be directed into both areas simultaneously; however, the suction pressure would be greater at the point of least resistance and would be less effective than directing the suction pressure to a selected point.

When using this system on non-ventilator patients, the trach collar would be in place around the patient's neck and would cover the Tracheostomy tube opening. An elastic cord that extends from the flanges of the collar would secure the collar in place. Inside the collar would be lumen tubing that would snap directly into the Tracheostomy tube. A the lower base of the collar would be a screen-like device that would help trap secretions prior to suctioning. Below this device would be the suction tubing adaptor. The dual press button adapter would have a split design that would direct suctioning to either the trach tube or the trach collar. The press button adapter would have two recessed press buttons that would direct the pressure to the desired location.

When using this system on ventilator patients, the swivel adapter would be used instead of the modified trach collar. The swivel adapter would be snapped in place directly over the head of Tracheostomy tube. Inside the new designed swivel adapter would be the internal suction connector 62 that would snap into the opening of the Tracheostomy tube. Positioned at the base of the swivel adapter would be suction tubing adapter. The press button then would be attached to suction tubing coming from the collection canister.

In both of the above-described applications, when the system is in place, negative suction pressure should be directed to the base of the Tracheostomy tube as desired, by merely pressing the suction button(s) on the press button adapter.

Due to the ease with which this system functions, the assembly creates a measured suction system which saves time for the care giver and decrease the risks and complications of deep tracheal suctioning for the patients.

The foregoing detailed description is given primarily for clearness of understanding and no unnecessary limitations are to be understood therefrom, for modifications will become obvious to those skilled in the art based upon more recent disclosures and may be made without departing from the spirit of the invention and scope of the appended claims.

We claim:

1. A tracheostomy tube comprising a stem and a head, said stem including a first primary channel for air flow extending the length of said tracheostomy tube, and a second channel extending contiguous and parallel to, and beneath said first channel, said second channel being closed at a lower distal end thereof, said first channel and said second channel sharing a common sidewall forming a barrier therebetween, said common sidewall including means therein for exchanging fluid between said first channel and said second channel, wherein said common sidewall forming a barrier comprises a porous membrane.

2. The tracheostomy tube of claim 1, wherein said common sidewall forming a barrier comprises a strip of material having holes therein.

3. The tracheostomy tube of claim 2, including a hand controlled suction line adapter for use with children and/or infants.

4. The tracheostomy tube of claim 3, including a trach cuff and pilot balloon for use with adults.

5. The tracheostomy tube of claim 1, including a trach collar.

6. The tracheostomy tube of claim 1, including a swivel adapter.

7. The tracheostomy tube of claim 1, including a swivel adapter and a press button adapter to facilitate suctioning of fluid from a base of said tracheostomy tube for use in conjunction with mechanical ventilation.

8. A tracheostomy tube comprising a stem and a head, said stem including a first primary channel for air flow extending the length of said tracheostomy tube, and a second channel extending contiguous and parallel to, and beneath said first channel, said second channel being closed at a lower distal end thereof, said first channel and said second channel sharing a common sidewall forming a barrier therebetween, said common sidewall including means therein for exchanging fluid between said first channel and said second channel;

a trach collar;

wherein said trach collar includes a dual press button adapter to facilitate suctioning of fluid from a collection base and/or suctioning fluid through a channel and a tube.

9. A tracheostomy tube said tracheostomy tube defining an upper and a lower end and having a selected portion thereof including means for partitioning separating the interior of said tracheostomy tube into two flow passages defining a first primary channel extending the length of said tracheostomy tube, and a second channel extending contiguous and parallel with said first primary channel, said second channel extending from said upper end to a selected point therealong, said second channel including a least one opening therethrough allowing passage of air and/or liquid fluid between said first primary channel and said second channel;

a trach collar;

wherein said trach collar includes a dual press button adapter to facilitate suctioning of fluid from a collection base and/or suctioning fluid through a channel and a tube.

10. The tracheostomy tube of claim 9, including a hand controlled suction line adapter for use with children and/or infants.

11. The tracheostomy tube of claim 9, including a trach cuff and pilot balloon for use with adults.

12. The tracheostomy tube of claim 9, including a swivel adapter for mechanical ventilation.

13. The tracheostomy tube of claim 9, including a swivel adapter and a press button adapter to facilitate suctioning of fluid from a base of said tracheostomy tube for use in conjunction with mechanical ventilation.

* * * * *